(12) United States Patent
Huizenga

(10) Patent No.: US 12,220,230 B2
(45) Date of Patent: Feb. 11, 2025

(54) DISTRIBUTED SYSTEM ARCHITECTURE FOR GAIT MONITORING AND METHODS OF USE

(71) Applicant: MOTERUM TECHNOLOGIES, INC., Greenville, SC (US)

(72) Inventor: David Huizenga, Greenville, SC (US)

(73) Assignee: MOTERUM TECHNOLOGIES, INC., Greenville, SC (US)

( * ) Notice: Subject to any disclaimer, the term of this patent is extended or adjusted under 35 U.S.C. 154(b) by 326 days.

(21) Appl. No.: 17/256,814

(22) PCT Filed: Jul. 3, 2019

(86) PCT No.: PCT/US2019/040522
§ 371 (c)(1),
(2) Date: Dec. 29, 2020

(87) PCT Pub. No.: WO2020/010212
PCT Pub. Date: Jan. 9, 2020

(65) Prior Publication Data
US 2021/0251518 A1 Aug. 19, 2021

Related U.S. Application Data

(60) Provisional application No. 62/693,627, filed on Jul. 3, 2018.

(51) Int. Cl.
*A61B 5/11* (2006.01)
*A61B 5/00* (2006.01)

(52) U.S. Cl.
CPC ............ *A61B 5/112* (2013.01); *A61B 5/0022* (2013.01); *A61B 5/1112* (2013.01); *A61B 5/6807* (2013.01); *A61B 2562/0219* (2013.01)

(58) Field of Classification Search
CPC ... A61B 5/0002; A61B 5/0022; A61B 5/1112; A61B 5/112; A61B 5/6807;
(Continued)

(56) References Cited

U.S. PATENT DOCUMENTS 9,295,302 B1 * 3/2016 Reed .................... A43B 3/128
2006/0252999 A1   11/2006 Devaul et al.
(Continued)

FOREIGN PATENT DOCUMENTS

| JP | 2006-102156 A | 4/2006 |
| JP | 2016-087346 A | 5/2016 |

(Continued)

OTHER PUBLICATIONS

Extended European Search Report issued in EP 19830173.1, dated Mar. 11, 2022, 7 pages.
(Continued)

*Primary Examiner* — May A Abouelela
*Assistant Examiner* — Anna Roberts
(74) *Attorney, Agent, or Firm* — Meunier Carlin & Curfman LLC

(57) ABSTRACT

The present disclosure relates to system and techniques for receiving data from one or more sensors associated with a person and controlling the use and redistribution of that data so it is used in an intended manner. In particular, the data is related to a gait and/or mobility of the person.

10 Claims, 5 Drawing Sheets

(58) Field of Classification Search
CPC .......... A61B 2562/0219; G16H 20/30; G16H 40/63; G16H 40/67; G16H 50/20; G16H 50/30
See application file for complete search history.

(56) References Cited

U.S. PATENT DOCUMENTS

| | | |
|---|---|---|
| 2010/0333116 A1* | 12/2010 | Prahlad .............. G06F 16/1844 713/153 |
| 2017/0010667 A1 | 1/2017 | Tanaka et al. |
| 2017/0035641 A1* | 2/2017 | Feger .................... A61B 5/112 |
| 2017/0055880 A1 | 3/2017 | Agrawal et al. |
| 2017/0185697 A1* | 6/2017 | Handzic ................ F16K 17/34 |
| 2017/0197115 A1* | 7/2017 | Cook ................. A63B 24/0075 |
| 2018/0126158 A1* | 5/2018 | Perez .................... A61B 5/1116 |
| 2018/0132758 A1* | 5/2018 | Benford ................ A61B 5/112 |

FOREIGN PATENT DOCUMENTS

| | | | | |
|---|---|---|---|---|
| WO | WO-2015164456 A2 * | 10/2015 | ........... | A43B 3/0015 |
| WO | WO-2017081647 A1 * | 5/2017 | ............. | A61B 5/112 |

OTHER PUBLICATIONS

International Search Report and Written Opinion issued in PCT/US2019/040522, dated Oct. 2, 2019, 10 pages.
Office Action received in related Japanese Application No. 2021-521936 mailed Mar. 22, 2023.
Office Action received in related Chinese Application No. 201980051275.9 mailed Nov. 30, 2023.

* cited by examiner

DISTRIBUTED SYSTEM ARCHITECTURE FOR GAIT MONITORING AND METHODS OF USE

CROSS-REFERENCE TO RELATED APPLICATION

This application is a national stage application filed under 35 U.S.C. § 371 of PCT International Application No. PCT/US2019/040522 filed on Jul. 3, 2019, entitled "DISTRIBUTED SYSTEM ARCHITECTURE FOR GAIT MONITORING AND METHODS OF USE." which claims priority to and benefit of U.S. provisional patent application Ser. No. 62/693,627 filed Jul. 3, 2018, which are fully incorporated by reference and made a part hereof.

TECHNICAL FIELD

The present disclosure relates to a system and method of gait monitoring and for wirelessly transmitting data relating to said monitoring, and controlling the display and distribution of that data.

BACKGROUND

Asymmetric gait is sometimes developed in individuals with central nervous system damage, such as stroke, or in persons who have suffered damage to the spinal cord, brainstem, cerebellum, or motor cortex. In such cases, a limp is developed and the person does not fully extend his foot far enough backward, which can prevent him from effectively pushing off into the swing phase of his gait.

In such cases, rehabilitation is often provided using gait-altering device such as, for example, a split-belt treadmill having two independent belts that can be operated at different speeds to exaggerate the asymmetry of the person's gait and/or a gait-altering shoe or shoes.

While these devices can help persons with asymmetric gaits, there is not a good way to continuously monitor a person when undergoing therapy or treatment involving gait-altering devices or to effectively use the information collected when performing such monitoring.

In view of the above discussion, it can be appreciated that it would be desirable to have a way to provide distributed system architecture for gait monitoring and methods of use.

The present disclosure is directed to overcoming the above and other challenges. While several examples of challenges that arise in a distributed system for gait monitoring are described, other problems and solutions are discussed below throughout the specification, and the scope of the claims should not be limited to addressing only challenges associated with gait monitoring.

SUMMARY

Described in this disclosure are systems and methods for gathering, analyzing and controlling the distribution and use of data (information) having multiple categories of sensitivity (e.g., restricted, less-restricted, etc.) throughout a distributed architecture. Exemplary embodiments allow data to be sent from one or more sensors to one or more intermediate devices and forwarded on to a cloud computing architecture. As noted herein, a number of challenges can arise with the distribution of data that has varying degrees of sensitivity such as medical data, including but not limited to limiting third-parties and certain system components from accessing restricted data such as proprietary, confidential or patient-identifying information while being selectively allowed to access other less-sensitive data, ensuring that unauthorized entities cannot access restricted data, and providing a system that can scale to receive, store, and selectively grant access to large amounts of data.

In one illustrative embodiment, the intermediate device separates data into multiple categories prior to transmission. The categories can be based on whether the data identifies a patient, contains proprietary information relating to system operation (e.g., error codes, calibration formulas, raw data, calibrated data, and the like), or contains information that third-parties and other system components can access. The categories will be referred to herein as public and private data. In other embodiments, a display or a cloud computing architecture can receive and separate the data into multiple categories. Then, the cloud computing architecture can separately store the data and restrict access to only one or more of the multiple categories of data based on the entity requesting access. Different systems can perform data synchronization at different times.

In other embodiments, different data streams containing different types of data can be sent separately to a server and stored separately. The data streams may be duplicative, such as where one or more sensors transmit a data stream to two connected intermediate devices, each of which forward their data (along with any other data generated by the display) to a server. This results in two separate data streams from two intermediate devices, which should be duplicative data. The cloud computing architecture stores the data streams separately, allowing it to easily grant or restrict access to the data, and also allowing the data streams to be compared to ensure correct system operation. In addition, each intermediate device can transmit multiple data streams where the data has been separated into one or more of the multiple categories as appropriate to allow for easy classification and permission-based access. For example, each intermediate device can send two data streams, resulting in the cloud computing architecture receiving four data streams associated with a single set of one or more sensors. The server can then resume transmission with each particular intermediate device based on the most recently received transmissions from that intermediate device.

The intermediate device may transmit the categories of data at the same or different times. For example, the intermediate device may transmit some data in real-time, such as every five minutes, and other data as part of a periodic bulk transfer, such as hourly. The cloud computing architecture separately stores the real-time and bulk data. In addition, different components within the cloud computing architecture store real-time and bulk data for differing durations. This allows quick access to more recent data, such as data generated in the last thirty days, without requiring that a single server store extremely large volumes of data. Instead, the cloud computing architecture stores long-term data in separate storage.

In other exemplary embodiments, the one or more sensors can encrypt at least some data prior to transmission. Encryption prevents unauthorized third-parties from accessing the data. The one or more sensors encrypt some or all of the data, and only intermediate devices authorized to access a particular type of data obtain the decryption key. For example, the one or more sensors transmit multiple pieces of data to an intermediate device, which only has a key to decrypt some of the data. The intermediate device forwards the data to a server that has a key used to decrypt some or all of the data. In this manner, the one or more sensors encrypt private data that remains encrypted during distribution through the system until receipt by a server.

Other exemplary embodiments address a common interface for accessing the described distributed system architecture. The system or system components can be an approved medical device that may require a new approval for certain changes to system design or operation. Yet, third parties will request access to the medical data and the third-parties will use a variety of different types of requests. As third-parties create new software applications and servers, changes would need to be made to the system to grant the requested access. For example, a third-party application requests access to mobility levels in the last week to integrate the mobility levels with information regarding food consumption. Another application requests access to mobility levels to provide recommendations on medical treatments. These applications could have different interfaces and request access to different types of data (e.g., real-time v. bulk, mobility levels with or without patient identifying information, etc.). To address these issues, the cloud computing architecture implements a hub and spoke topology that provides a set of common application program interfaces. The third parties can interface with the common application program interfaces that have been granted regulatory approval. In addition, the system provides a user with a single sign-on so the user does not need to log into separate systems as a user accesses various system modules.

In addition, exemplary embodiments control access to a patient's medical information by remote monitors of a specific patient. A remote monitor is a device under control of a person other than the patient using a gait-altering device who has access to at least some gait information for the patient. For example, a child or sibling can follow a patient's mobility and/or gait progress using a remote monitor. Maintaining confidential person-identifying information by system components can be problematic because the information may fall under HIPAA and other regulations. This could include information identifying the remote monitors themselves and location or other information identifying the remote monitors. To avoid storing identifying information about a remote monitor, the remote monitor can register with the system through an anonymous identifier generator and the system can store, for example, a unique number that associates an anonymous identification of the remote monitor with a display device. The cloud computing architecture therefore does not need to receive or store any specifically identifying information for a remote monitor.

In one aspect, a method for securely transmitting data relating to gait and/or mobility is described. The method can comprise preparing data including gait information using one or more sensors; wirelessly transmitting the gait information to at least one intermediate device from the one or more sensors; forwarding the gait information from the intermediate device to a cloud computing architecture; storing the gait information in one or more (separate) groups at the cloud infrastructure; analyzing at least a portion of the information related to the gait of the person; and providing access to at least a portion of the analyzed information to one or more devices In another aspect, a system for monitoring a gait of a person is disclosed. The system can comprise a one or more sensors configured to prepare data relating to a person's gait; an intermediate device configured to receive the transmitted gait information and forward the data; and a cloud computing architecture configured to receive the forwarded data and store the data, wherein one or more servers in the cloud computing architecture analyze at least a portion of the information related to the gait of the person; and provide access to at least a portion of the analyzed information to one or more devices.

In yet another aspect of the present disclosure, a computer-readable media comprising instructions which, when executed by one or more processors, perform a method for securely transmitting gait information is described. The instructions can comprise preparing data relating to gait information using one or more sensors; wirelessly transmitting the gait information to at least one intermediate device; forwarding the gait information from the intermediate device to a cloud computing architecture; storing the data relating to gait information in the cloud infrastructure; analyzing at least a portion of the information related to the gait of the person; providing access to at least a portion of the analyzed information to one or more devices Other systems, methods, features and/or advantages will become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

The present disclosure relates to techniques for receiving gait and/or mobility data from one or more sensors and controlling the use and redistribution of that data so it is used in an intended manner.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Figure 1A:
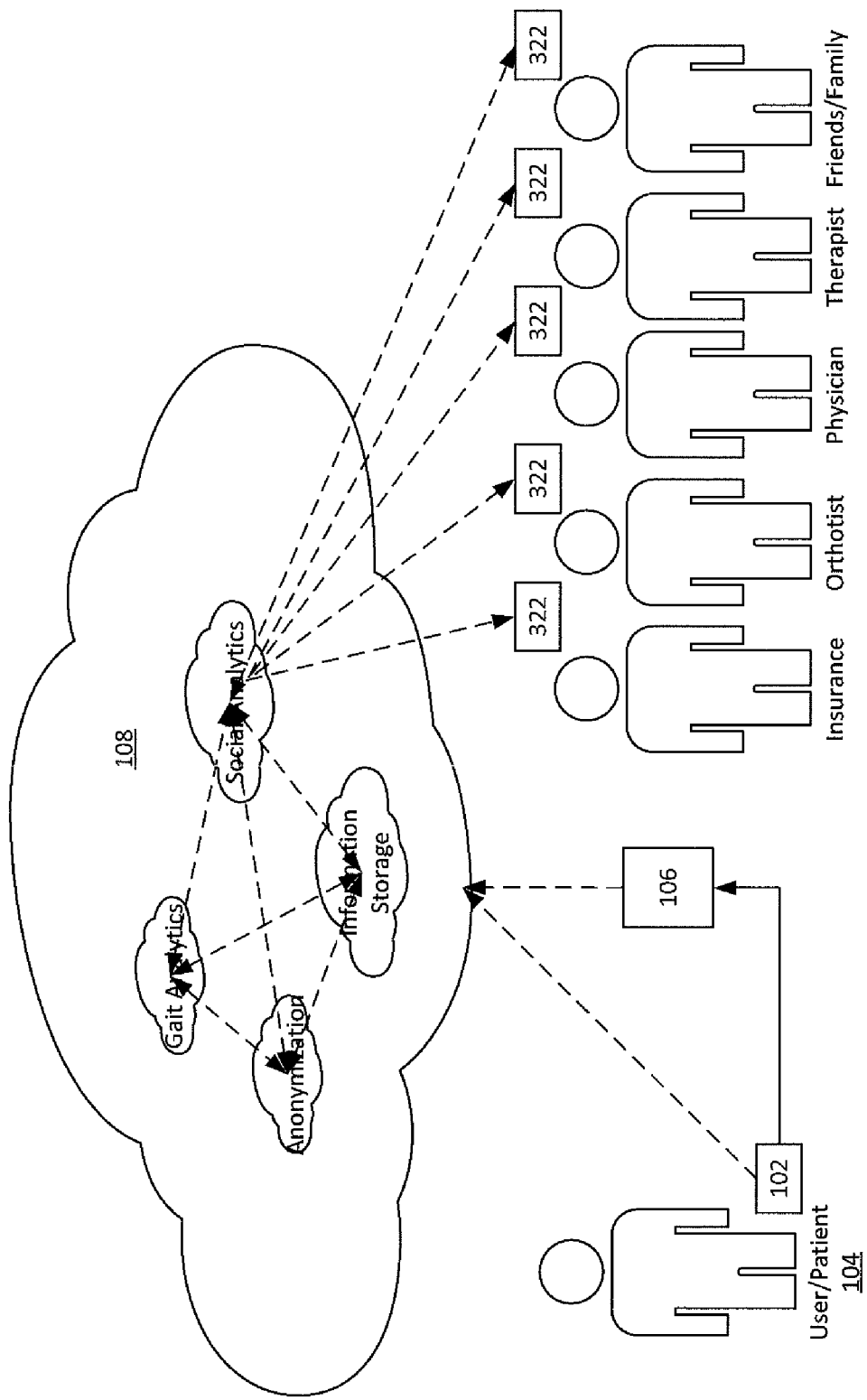
FIG. 1A illustrates an exemplary system for monitoring gait and/or mobility information and controlling access to and use of the information.

FIG. 1A illustrates an exemplary system for monitoring gait of a person and use of data associated with such monitoring. Such data can be defined as having multiple categories, with each category having one or more levels of sensitivity. The disclosed system of FIG. 1A can be used for storing and distributing data, wherein data in different categories or having different levels of sensitivity can be treated differently within the system. For example, data that identifies or can be used to identify a patient should not be reproduced to all third-parties. Only third-parties having proper permissions or authorizations should be able to access this data. Furthermore, other data, such as mobility information associated with a specific person, can be misused by third parties. As an example, third-parties receiving monitored gait information might make incorrect recommendations to a user on how to control a gait-altering device. The system of FIG. 1A allows some data to be treated differently than others by separating categories of data, such as public data, private data, real-time data (raw or calibrated), and other bulk data. The system of FIG. 1A can allow some data to be treated differently than other by offering permission-based access to data. Furthermore, the system of FIG. 1A can store and provide access to large amounts of data. For example, the system of FIG. 1A can temporarily store some data in a cloud computing architecture 108, such as data within the a most recent definable time period (e.g., 15 days, 30 days, 60 days, etc.), and periodically transfer other data, such as data aged more than thirty days, to longer-term storage.

Figure 1B:
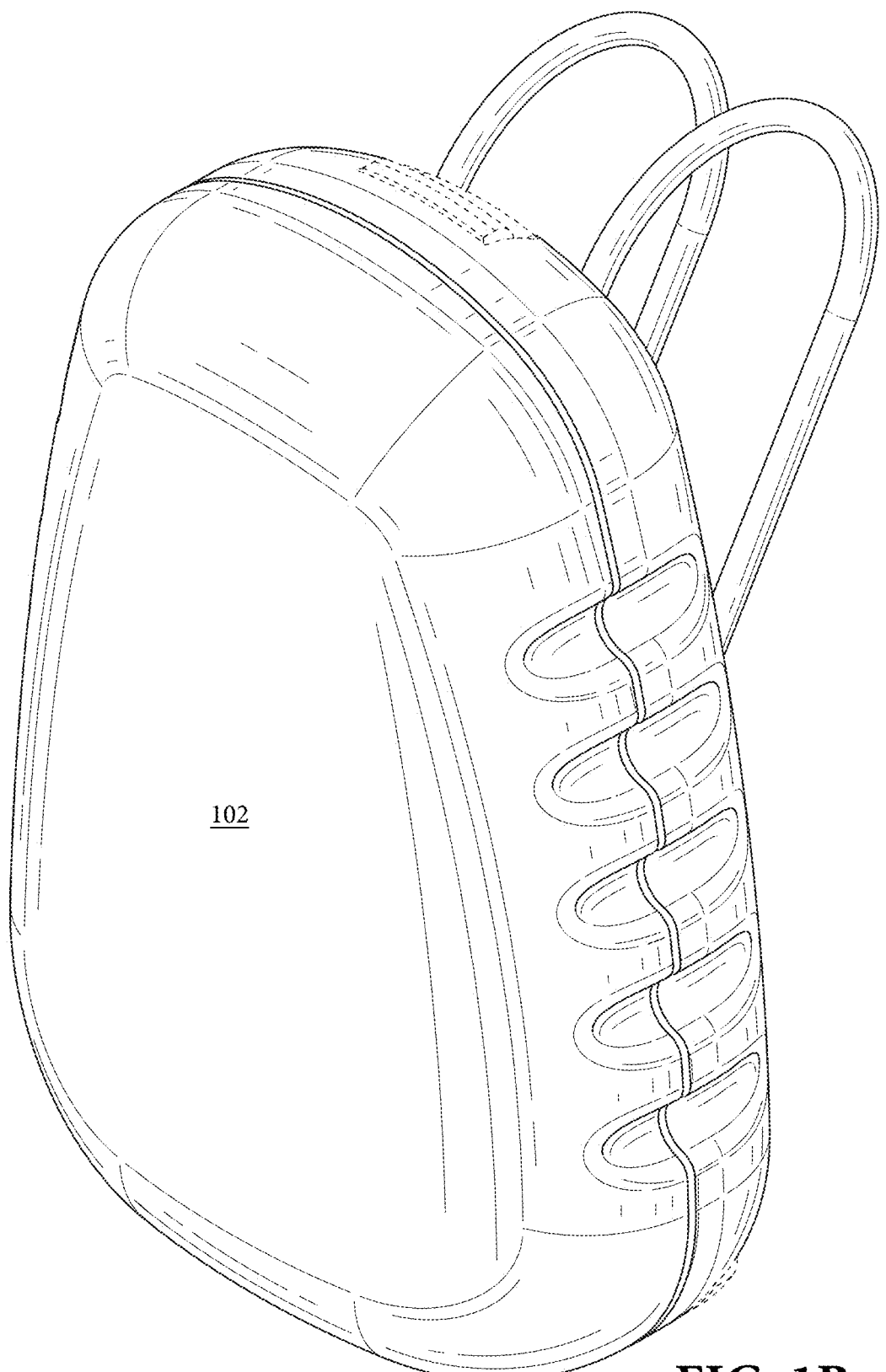
FIG. 1B illustrates an image of a sensor that can be attached to a gait-altering device or otherwise attached to a person to gather data about a person's gait.

With reference to FIG. 1A, one or more sensors 102 obtain a series of measurements relating to a gait of a patient 104 (herein, a patient may also be equivalently referred to as a "user" and/or a "person" and/or a "wearer," and the like). In some instances, the one or more sensors 102 may be associated with a gait-altering device. One non-limiting example of a gait-altering device are the gait-altering shoes that are described in U.S. Pat. No. 9,295,302 issued Mar. 29, 2016, which is fully incorporated by reference. In some instances, at least one of the sensors 102 may be incorporated into the gait-altering device, while others may be worn by the patient 104 or be proximate to the patient 104. FIG. 1B is an image of a sensor 102 that can be attached to a gait-altering device or otherwise attached to a person to gather data about a person's gait. Non-limiting examples of the sensors 102 include one or more of an accelerometer, a barometer, a gyroscope, a position-detection device such as a GPS unit, a video camera, sensors that monitor physiological aspects of the patient 104 such as blood-pressure sensors, pulse/heart rate sensors, blood-oxygen level sensors, temperature, and the like.

In some instances, information obtained by the one or more sensors 102 is transferred to an intermediate device 106 using a communications interface. This transfer may occur through wires (including fiber optics) and/or be transferred wirelessly. The intermediate device 106 can be, for example, dedicated receivers associated with the one or more sensors 102, smart phones, smart watches, personal computers, tablets, and a variety of other computing devices. Although not illustrated, sensors 102 may include nonvolatile memory for storing historical data, a processor, a battery, and a wireless transmitter. The wireless transmitter can provide any type of wireless communications, including a Bluetooth® connection, Wi-Fi connection, RF connection, and others, with the intermediate device 106 and other computing devices. The wireless communications occur, in some embodiments, between paired, authenticated devices, and use encryption and other cryptographic techniques to ensure that communications remain confidential. In other instances, the sensors 102 may include a wireless transmitter capable of communicating directly with a network without use of an intermediate device. For example, the sensors 102 may be connected with a Wi-Fi transceiver that can communicate wirelessly with a LAN, WAN, or other type of network. Alternately or optionally, the sensors 102 may be connected to a wireless transceiver that enable communications directly with a network such as a cloud computing network.

While illustrated as a single unit, portions of the intermediate device 106 may be removable from remaining portions of the intermediate device 106. For example, reusable electronics portions of the intermediate device 106 (e.g., transmitter, battery, memory) may be removable from single use portions of the intermediate device 106 (e.g. and reused with a new single use portion). Further, the intermediate device 106 can include other components to facilitate data communications. For example, the intermediate device 106 may include wired ports, such as a USB port, Ethernet port, and others, for communicating with other devices and providing data.

The one or more sensors 102 of FIG. 1A can obtain samples at real-time and/or at predetermined intervals, such as every few seconds, every thirty seconds, every minute, every five minutes, or on demand in response to the occurrence of an event (e.g., a command from a user, detection of a user action, such as user movement, and the like). The wireless transmitters of the one or more sensors 102 may in some instances be turned off or put into a low power state to conserve battery life while one or more measurements are taken over a period of time, and then wake the transmitter back up to wirelessly transmit the one or more measurements to the intermediate device 106 in a batch transfer.

The data transmitted between the one or more sensors 102 and the intermediate device 106 can be any type of data relating to monitoring a person 104 and, in particular to the monitoring of a gait of a person 104. Transmitted data may also include operation information of the one or more sensors 102, the wireless transmitter or transceiver, battery life, and the like. For example, the one or more sensors 102 may exchange calibration data with respective intermediate device 106 on initial startup and periodically to maintain accuracy of the measurements.

Other examples of data exchanged may include an amount of current or voltage (e.g., raw values) measured by a sensor 102, a timestamp associated with the time when each measurement or value was sampled, alerts related to set values exceeding/falling below predetermined thresholds, detected faults in the system, firmware version, hardware version for the sensor 102 and transmitter, calibration status, the time the senor was started and/or stopped, battery voltage, encryption information, a transmitter identifier number, and the like.

In some instances, the intermediate device 106 may be omitted, and all or a portion of the data may be transmitted directly from some or all of the one or more sensors 102 directly to a network such as the cloud computing architecture 108 using wireless communications technology. For example, the sensors 102 may be connected with a cellular chip that uses a modem to transfer data. Or, as described herein, the sensors 102 may connected with a wireless transceiver such as a Wi-Fi transceiver, a Bluetooth® transceiver, and the like. In some instances, there may be at least two data streams—that that is transmitted directly from a sensor 102 to the cloud computing architecture 108 and that which is transmitted to the intermediate device 106 and then from the intermediate device 106 to the cloud computing architecture 108. Any data of any type transmitted between the one or more sensors 102 and intermediate device 106, or between the intermediate device 106 and the distributed cloud computing architecture 108 or between any one the one or more sensors 102 and the intermediate device 106 and any other physiological monitoring device or any other system, device or person can be considered a data point.

Intermediate device 106 may be a device dedicated to use with the one or more sensors 102, or it may be a device having multiple uses. The combination of the one or more sensors 102 and an intermediate device 106 can, in one embodiment, be an approved medical device, such as a class III medical device.

Intermediate device 106 may include a processor for performing calculations based on received measurements, memory for storing information, ports for wired communications, and wireless communication circuits, such as Bluetooth®, Wi-Fi, or RF circuits. Intermediate device 106 may also be associated with a personal computer, tablet, or smart phone that executes applications. As a result, intermediate device 106 may include hardware components typically associated with personal computing devices, including processor(s), memory, wireless connections, a USB port, and others.

Intermediate device 106 can be a dedicated device or a general-purpose computing device, such as, for example, a smart phone. The smart phone can execute applications dedicated for use with the one or more sensors 102 and other applications. The dedicated application controls the distribution of medical data received from the one or more sensors 102 to other applications executing on the intermediate device 106 to preserve confidentiality and user preferences, as described in more detail below. The dedicated application can also be connected to and provide information to other third-party applications.

Figure 2:
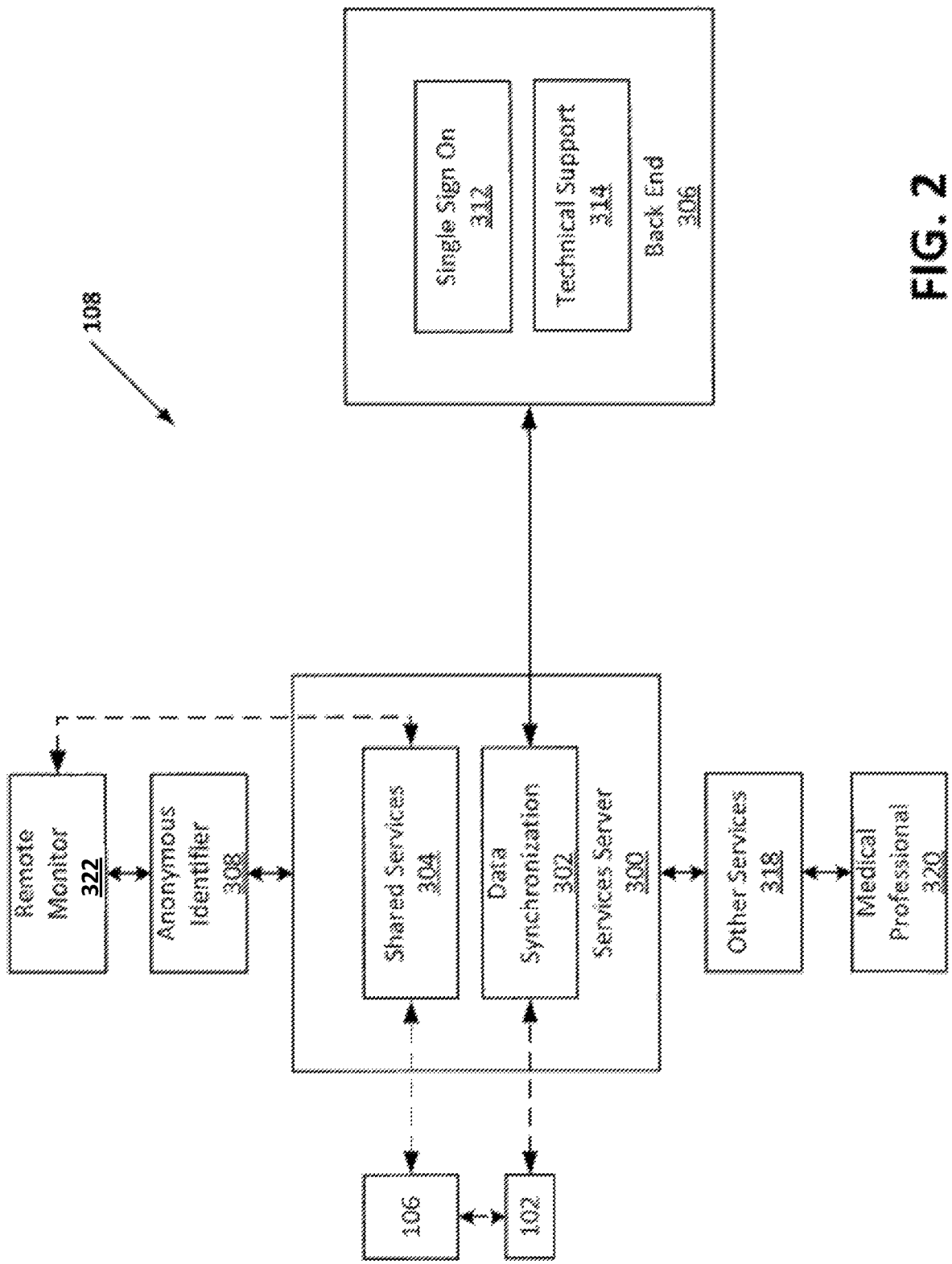
FIG. 2 illustrates an exemplary cloud computing architecture.
Figure 3:
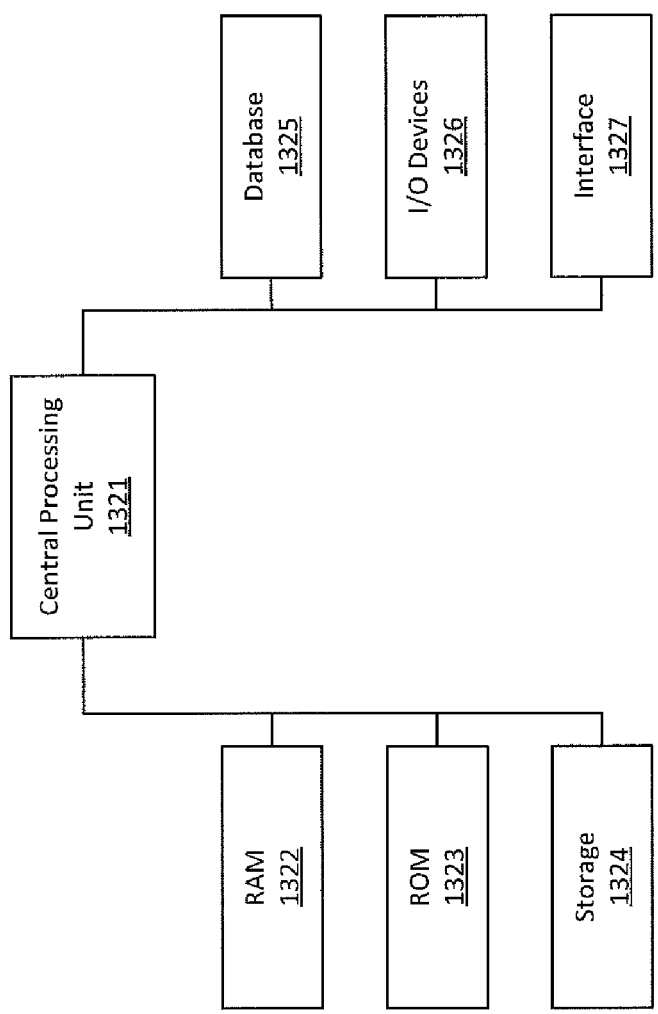
FIG. 3 illustrates an exemplary computer for use with the disclosed embodiments.

The intermediate device 106 and/or the one or more sensors 102 can transmit data to the distributed cloud computing architecture 108. The distributed cloud computing architecture 108 organizes, stores, analyzes, and provides access to the data by other computers, applications, and third-parties. The distributed cloud computing architecture 108 includes plurality of different servers, storage systems, and software applications executing both locally and across distributed networks. FIGS. 2 and 3 provides more detailed description of distributed cloud computing architecture 108.

Communications within the system can be subject to a number of security protocols. For example, communications can be encrypted and secured, such as HTTPS and SSL communications. The cloud computing architecture 108 may include a firewall that only allows specific and secure communication on defined ports. In addition, the system can use authenticated sessions with a login with name and password for web service methods that a user or remote monitor (described herein) would use to gain access to read or alter their information. The login names and passwords are stored in a secure fashion using hashing and encryption, and patient data including all data posts from the displays can be likewise encrypted and stored in a secure fashion by the cloud computing architecture 108.

Another security measure includes using an authenticated session that times out after a short period of inactivity and also can have a maximum length. Servers can keep an audit trail or history log of all access to the system and all changes made to the system. In addition, third parties accessing data stored by the cloud computing architecture can be required to authenticate themselves and may also be further restricted to only access patients they already know. That is, a consumer's privilege may require them to already know the patient's internal identifier with the system which would have already been provided by a patient initiated exchange of any identifying information with that consumer.

All of the data can be stored separately in data streams on both or either of the intermediate device 106 and the cloud computing architecture 108. This allows for an audit trail to determine what data came from which device and when. The cloud computing architecture 108 may separately store data received from each intermediate device 106 or data specific to a patient 104. The data can be stored using metadata by providing a timestamp at which time the data was received at or posted to the cloud computing architecture 108. Accordingly, the cloud computing architecture 108 can track the time at which the last post was received from a particular intermediate device 106 and/or sensor 102. The post might contain new data or data that was previously sent, dropped in transmission due to an error or other system malfunction, and then retransmitting. Metadata allows the intermediate device 106 and/or sensor 102 and the cloud computing architecture 108 to track the last attempted message transmission from the intermediate device 106 and/or sensor 102 and received message transmission by the cloud computing architecture 108. The servers therefore need not examine the actual data that was transmitted but instead rely on the metadata to efficiently store and subsequently retrieve information.

When new data records are created in the system, multiple other computers, devices and services, having proper permissions or authorizations, can be alerted about this data by requesting notifications from the cloud computing architecture. For example, a remote monitor 322 can receive information about mobility of the patient 104 by requesting notification of mobility/gait information for a specific patient 104 through the cloud computing architecture 108. These third-party applications can therefore obtain public information, including the mobility information, or other information that they have been provided authorization to receive, whereas a technical support team can also access proprietary private data.

FIG. 2 illustrates an exemplary cloud computing architecture 108. There are a number of challenges associated with receiving and storing large volumes of data. One such challenge is simply the volume of data. Receiving data from intermediate device 106 and/or sensor 102 in real-time or on a periodic basis, such as every five minutes, presents a large load on servers to store the data. This may be compounded by thousands of additional displays associated with other patients all transmitting data to the same server. The cloud computing architecture 108 can both, store long-term data that can be used by third-parties, technical support, and other systems, and provide fast access for recent data from a large number of patients. In addition, security issues arise for receiving the data and storing it in a secure fashion, and ensuring that only authorized devices obtain access to the data. Further, some data will be sent through a display but it may be desired that the display not be able to access it. An example is system diagnostic information sent from a transmitter to a server via a phone that can be used by technical support but is proprietary and should not be displayed to a user. The system of FIG. 2 allows different data to be treated differently, with varying levels of access by different system components.

In FIG. 2, intermediate device 106 and/or sensor 102 transmit data to services server 300. The services server 300 provides the functions for coordinating storage, retrieval, and notifications relating to gait information in the system. In one embodiment, the intermediate device 106 and/or sensor 102 transmit data to the services server 300 using, for example, HTTPS web services. The data includes, for example, gait cycle duration, gait cadence, stride length, stride velocity, turning angle, stance, swing, loading, foot flat, pushing, double support, peak angular velocity, swing speed, strike angle, lift-off angle, swing width, 3D path length, maximum heel clearance, maximum toe clearance (foot with toes angled downward), minimum toe clearance, and second maximum toe clearance (foot with toes angled downward), and other types of information such as exercising information or other health-related information. The intermediate device 106 and/or sensor 102 send the data to the services server 300 automatically in one embodiment. The data includes data from the one or more sensors 102 as well as any additional data added by the intermediate device 106.

Real-time data can be provided, for example, as it occurs (real-time or near real-time) and/or periodically (e.g., every five minutes) from intermediate device 106 and/or sensor 102. Bulk data can be provided, for example, in real-time or periodically such as once every hour from intermediate device 106 and/or sensor 102. Bulk data includes internal system data, such as system operation data, that typically would not be provided to any third-parties. The real-time data and bulk data points can be different or overlapping. For example, bulk data can also include gait information that are also real-time data values. The data can be sent directly from an intermediate device, such as a smart phone, or from the intermediate device 106 and/or sensor 102 to a personal computer or other computing device that uploads the data to the services server 300. For example, the intermediate device 106 can be a personal computer, and the personal computer uploads data through a wired or wireless link. In other embodiments, the intermediate device 106 can be a dedicated display associated with the one or more sensors 102 that is placed in a cradle. The cradle includes a network connection for uploading data to services server 300. In another embodiment, intermediate device 106 is a smart phone and it uploads data using an application. The real-time and bulk data can be synchronized with the services server 300 in different manners, such as at different time intervals, to facilitate separate storage and retrieval of real-time and bulk data by the cloud computing architecture 108.

In one embodiment, the transmitter of the intermediate device 106 and/or sensor 102 can encrypt all or a portion of the bulk data and pass it through the intermediate device 106 and/or sensor 102 to a services server 300 (see FIG. 2) using a key stored on the transmitter. The transmitter can also encrypt all or a portion of the real-time data using, for example, Bluetooth® encryption or other techniques, and the intermediate device 106 can receive the real-time data, decrypt some or all of it for use and display, and forward the realtime data to the services server 300 for storage.

Referring to FIG. 2, services server(s) 300 stores data for a predetermined amount of time, such as thirty days, and synchronizes data to other devices, applications, and outside companies, along with the back-end 306. The services server 300 and back-end 306 can employ different levels of security for different types of data. The services server(s) 300 includes shared services server 304. Shared services server(s) 304 store the real-time data separately from the bulk data. The displays can send the data separately or together, and the data can be separated into real-time and bulk data by the intermediate device 106 and/or sensor 102, or the services servers. In one embodiment, the shared services server 304 stores data for only a predetermined amount of time. This allows fast searching and access to shared data, and also limits the amount of data stored on shared services server 304. For example, shared services server 304 only stores the data for past 30 days, allowing data to be stored for only as long as other devices would need to retrieve the data. In other aspects, the shared services server 300 can store data for time periods greater than or less than 30 days.

The services server 300 supports gathering the data posts on a patient-by-patient, and stream-by-stream basis. A client, such as an intermediate device 106 and/or sensor 102, other service 318, remote monitor device 322, or other system component can subsequently request data by asking for a specific range of data for each patient. The range of data can be based on the time the data was posted to the server. In one embodiment, each transmission of data by a display can be assigned to a posting identifier. A request can be made to obtain all data posts that came after a posting identifier that can also be tracked by the client.

The system can maintain separate record "streams" of posted information for each patient's source display, such as a smart phone and a receiver dedicated to use with the intermediate device 106 and/or sensor 102. Each post can identify the source type by indicating which display posted the data. This will lead to duplicate posting of patient data, from multiple sources. The services server 300, in one embodiment, separately stores these streams of data posts to reduce the complexity on the posting display devices by allowing the display devices to create incremental posts relative only to their own self-contained contiguous data. Consumers may then maintain or report on the differences between the streams or may combine the contents of the streams as desired/required.

Examples of other devices that would access recent data through shared services server 304 include remote monitors 322 that receive data, alerts, information, and the like in real-time. A remote monitor 322 can be under the control of a person who monitors the gait and/or mobility levels of another patient. For example, one or more of an insurance provider, an orthotist, a physician, or a therapist, a family-member of the person, or anyone else designated by the person can monitor gait and/or mobility levels of a person 104 using a remote monitor 322.

One challenge that may arise with remote monitors 322 is that storing any identifying information for the remote monitor could place those interactions under government privacy laws and regulation such as, for example, HIPAA regulations. It would be preferable to avoid storing non-patient (i.e., remote monitor 322) information in the cloud computing architecture to avoid implicating any privacy law or regulation. Accordingly, in one embodiment the cloud computing architecture 106 need not receive or store any of a remote monitor's personal information. Instead, in one embodiment the remote monitor 322 can be assigned a digital signature or other secure anonymous identifier 308 that is associated with the remote monitor 322, but the relationship is not stored in the cloud computing architecture. For example, the registration process for a remote monitor 322 can result in the generation of a unique number that is an anonymous identification of the follower. Communications within the system, such as between the shared services server 304 and a remote monitor device 322 use the anonymous identifier 308 instead of information that would identify the remote monitor 322.

The cloud computing architecture 108 may also include back-end server(s) 306. The back-end 306 receives real-time data from shared services servers 304 and bulk data from data synchronization server 302. Back-end 306 stores historical data over thirty days old and receives requests for access to data through other services 318 that is more than thirty days old.

The back-end 306 functions as a data warehouse that can store data either permanently or for longer periods of time for archival purposes. Technical support unit 314 provides technical support to users and patients for any issues with system operation. Technical support unit 314 receives gait/mobility data and other real-time and bulk data and can permanently store the data to assist with future technical support issues. For example, a patient establishes alerts on intermediate device 106 and/or sensors 102 for when gait thresholds cross a defined level or experience a defined rate of change.

Single sign on server 312 provides a single sign-on for patients and users accessing a number of different applications and the system. If the system were comprised of separate systems, applications, and components, the user experience may not be seamless, as the user would need to log into separate systems. Accordingly, the smart phones and other displays can log into the system through the cloud infrastructure 108 using single sign on server 312. In one example, a transmitter identifier can be printed on an intermediate device 106 and used as the sign on to correlate a transmitter with a particular patient. In addition, users can have a login name and password, and a variety of different encryption algorithms can be used in the authentication process.

Other services 318 can include a number of other services that seek access to patient data. As an example, a medical professional (e.g., doctor) 320 can request access through other services 318 to patient data stored by services server. The other services 318, in one embodiment, receive real-time data through services server 300 for the past thirty days. Other services 318 can synchronize data and save data periodically through services servers 300. For example, some other applications can request data hourly, others daily, and others weekly to have the data from services servers 300. For example, other services 318 can include applications that request data to perform data analytics, both for individual patients and for classes of patients. When other services 318 request data beyond the age range stored by services servers 300, that request is sent to and processed by back-end 306, which stores longer-term archived bulk and real-time data. The timing as to when various components of the system can request access to bulk and real-time data can vary. For example, the cloud computing architecture can restrict other services 318 to only accessing data once per day, allowing full access at any time, or on a variety of other timeframes.

It will be appreciated that the cloud computing architecture 108 of FIGS. 1A and 2 can include fewer or additional components. In addition, the system can include a plurality of cloud computing architectures so that fewer than all of the displays transmit data to a single cloud computing architecture. For example, a plurality of connected cloud computing architectures can be used throughout different geographical regions, although other arrangements are also possible to distribute the computing load.

As noted above, in some instances the patient 104 is wearing and/or using a gait-altering device. In some instances, the gait-altering device may comprise a gait-altering shoe, said gait-altering shoe comprising a frame adapted to support a user's foot; and at least one wheel that supports the frame above a walking surface, the wheel having a radius that varies as a function of angular position of the wheel such that the wheel automatically rotates when weight is applied to the shoe. In some instances, an aspect of the gait-altering shoe may be modified based on at least a portion of the analyzed information. For example, modifying the aspect of the gait-altering shoe based on at least a portion of the analyzed information may comprise providing a new wheel with a design based at least in part on the portion of the analyzed information. Designing such a new wheel may be performed as described in international patent application publication no. WO 2015/123451 A1, published Aug. 20, 2015, which is fully incorporated by reference.

FIG. 3 illustrates an exemplary computer. Sensors 102, intermediate device 106, the cloud computing architecture 108 and associated servers, as well as other system components, can include all or some of the components shown in FIG. 3.

The computers may include one or more hardware components such as, for example, a central processing unit (CPU) 1321, a random-access memory (RAM) module 1322, a read-only memory (ROM) module 1323, a storage 1324, a database 1325, one or more input/output (I/O) devices 1326, and an interface 1327. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 1324 may include a software partition associated with one or more other hardware components. It is understood that the components listed above are exemplary only and not intended to be limiting.

CPU 1321 may include one or more processors, each configured to execute instructions and process data to perform one or more functions associated with a computer for monitoring gait and/or mobility levels. CPU 1321 may be communicatively coupled to RAM 1322, ROM 1323, storage 1324, database 1325, I/O devices 1326, and interface 1327. CPU 1321 may be configured to execute sequences of computer program instructions to perform various processes. The computer program instructions may be loaded into RAM 1322 for execution by CPU 1321.

RAM 1322 and ROM 1323 may each include one or more devices for storing information associated with operation of CPU 1321. For example, ROM 1323 may include a memory device configured to access and store information associated with the computer shown in FIG. 3, including information for identifying, initializing, and monitoring the operation of one or more components and subsystems. RAM 1322 may include a memory device for storing data associated with one or more operations of CPU 1321. For example, ROM 1323 may load instructions into RAM 1322 for execution by CPU 1321.

Storage 1324 may include any type of mass storage device configured to store information that CPU 1321 may need to perform processes consistent with the disclosed embodiments. For example, storage 1324 may include one or more magnetic and/or optical disk devices, such as hard drives, CD-ROMs, DVD-ROMs, or any other type of mass media device.

Database 1325 may include one or more software and/or hardware components that cooperate to store, organize, sort, filter, and/or arrange data used by CPU 1321. For example, database 1325 may data relating to monitoring gait and/or mobility levels, associated metadata, and health information. It is contemplated that database 1325 may store additional and/or different information than that listed above.

I/O devices 1326 may include one or more components configured to communicate information with a user associated with the device shown in FIG. 3. For example, VO devices 1326 may include a console with an integrated keyboard and mouse to allow a user to maintain a database of images, update associations, and access digital content. VO devices 1326 may also include a display including a graphical user interface (GUI) for outputting information on a monitor. VO devices 1326 may also include peripheral devices such as, for example, a printer for printing information associated with the computer shown in FIG. 3, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1327 may include one or more components configured to transmit and receive data via a communication network, such as the Internet, a local area network, a workstation peer-to-peer network, a direct link network, a wireless network, or any other suitable communication platform. For example, interface 1327 may include one or more modulators, demodulators, multiplexers, demultiplexers, network communication devices, wireless devices, antennas, modems, and any other type of device configured to enable data communication via a communication network.

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object-oriented programming language such as Java®, Smalltalk™, C++, or the like, and conventional procedural programming languages, such as the "C" programming language or similar programming languages. The program code may execute entirely on the computing unit.

Figure 4:
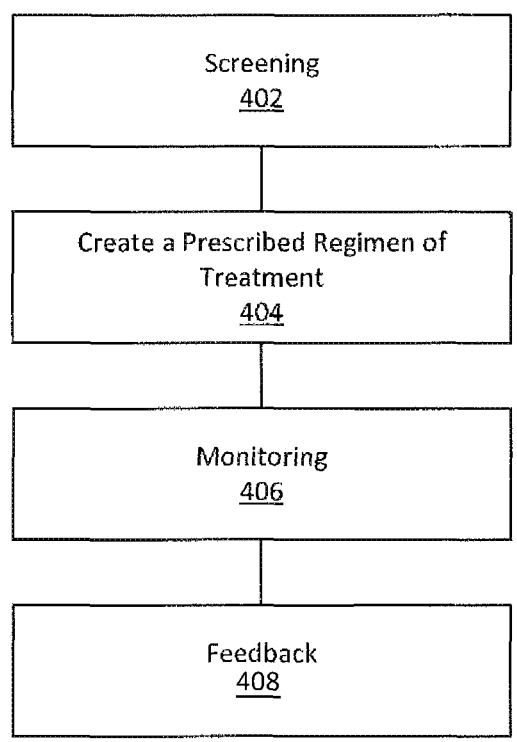
FIG. 4 is a flowchart describing an exemplary method of use of the disclosed systems and components.

FIG. 4 is a flowchart describing an exemplary method of the disclosed systems and components. In FIG. 4, a person having a medical condition is screened 402. The screening may be performed, for example, by a medical professional or, in some instances, it may be a self-administered electronic screening that the person (or someone close to the person) performs by answering questions and/or performing tasks that are entered or recorded into a computing device (e.g., smartphone, computer, etc.). In turn, at 404 the computing device either executes an algorithm or passes the received information to a server that executes the algorithm that creates a prescribed regimen of treatment using the gait-altering device based on the entered information. At 406, the person's use (or lack of use) of the gait-altering device is monitored using the sensors and systems described herein. The data from the monitored use of the gait-altering device is compared to the prescribed regimen of treatment and at 408 feedback is provided to the person, medical professionals, authorized family/friends or others.

It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. A method of monitoring a gait of a person, said method comprising:
    placing a gait-altering device on at least one foot of a person;
    attaching a transferable housing to the gait-altering device, wherein the transferable housing contains all of a plurality of wireless sensors that monitor a gait of the person;
    obtaining, using the plurality of wireless sensors of the transferable housing that monitor a gait of the person, first sensor data while the person is wearing the gait-altering device;
    transforming the first sensor data obtained from the plurality of wireless sensors into one or more of first gait parameters wherein the one or more of first gait parameters includes one or more of gait cycle duration, gait cadence, stride length, stride velocity, turning angle, stance, swing, loading, foot flat, pushing, double support, peak angular velocity, swing speed, strike angle, lift-off angle, swing width, 3D path length, maximum heel clearance, maximum toe clearance (foot with toes angled downward), minimum toe clearance, and second maximum toe clearance (foot with toes angled downward) while the person is wearing the gait-altering device;
    removing the gait-altering device from the at least one foot of the person;
    removing the transferable housing from the gait-altering device and attaching the transferable housing to the at least one foot of the person;
    obtaining, using the plurality of wireless sensors of the transferable housing that monitor the gait of the person, second sensor data while the person is not wearing the gait-altering device and has the transferable housing attached to the at least one foot;
    transforming the second sensor data obtained from the plurality of wireless sensors into one or more of second gait parameters wherein the one or more of second gait parameters includes one or more of gait cycle duration, gait cadence, stride length, stride velocity, turning angle, stance, swing, loading, foot flat, pushing, double support, peak angular velocity, swing speed, strike angle, lift-off angle, swing width, 3D path length, maximum heel clearance, maximum toe clearance (foot with toes angled downward), minimum toe clearance, and second maximum toe clearance (foot with toes angled downward) while the person is not wearing the gait-altering device;
    analyzing, by one or more processors, at least a portion of the first gait parameters and the second gait parameters, wherein the analyzing at least comprises comparing at least a portion of the first gait parameters and the second gait parameters; and
    determining, by the one or more processors, based on the analysis, a treatment plan and/or a modification of an existing treatment plan for the person involving use of the gait-altering device,
    wherein the gait-altering device comprises a gait-altering shoe comprising a frame adapted to support the at least one foot of the person; and at least one wheel that supports the frame above a walking surface, the wheel having a radius that varies as a function of angular position of the wheel such that the wheel automatically rotates when weight is applied to the shoe.

2. The method of claim 1, wherein the one or more processors comprise at least a portion of a cloud network, wherein the cloud network includes cloud storage, and at least a portion of the first sensor data and/or the first gait parameters related to the gait of the person while wearing the gait-altering device and at least a portion of the second sensor data and/or the second gait parameters related to the gait of the person while not wearing the gait-altering device is stored in the cloud storage.

3. The method of claim 1, wherein the plurality of wireless sensors comprise at least of an accelerometer, a gyroscope, a barometer, and a GPS detection device.

4. The method of claim 1, wherein analyzing, by the one or more processors, at least the portion of the first gait parameters and the second gait parameters, further comprises comparing at least a portion of the first gait parameters obtained at a first time to at least a portion of the first gait parameters obtained at a second time and/or comparing at least a portion of the second gait parameters obtained at a first time to at least a portion of the second gait parameters obtained at a second time, wherein the first time and the second time are not the same.

5. The method of claim 1, further comprising modifying an aspect of the gait-altering shoe based on at least a portion of the analyzed first gait parameters and/or second gait parameters, wherein modifying the aspect of the gait-altering shoe based on at least a portion of the analyzed first gait parameters and/or second gait parameters comprises providing a new wheel with a design based at least in part on the portion of the analyzed first gait parameters and/or second gait parameters.

6. The method of claim 1, further comprising providing, by the one or more processors, access to at least a portion of the analyzed first gait parameters and/or second gait parameters to one or more devices, wherein the one or more devices comprise one or more devices controlled by authorized persons authorized by the person.

7. A system comprising:
a gait-altering device, wherein the gait-altering device comprises a gait-altering shoe comprising a frame adapted to support at least one foot of a person; and at least one wheel that supports the frame above a walking surface, the wheel having a radius that varies as a function of angular position of the wheel such that the wheel automatically rotates when weight is applied to the shoe;
a plurality of wireless sensors configured to monitor a gait of the person's gait, wherein the plurality of wireless sensors are all contained within a transferable housing; and
one or more processors, wherein the one or more processors:
receive from the plurality of wireless sensors, first sensor data comprising data obtained from the plurality of wireless sensors while the person is wearing the gait-altering device, wherein the transferable housing is attached to the gait-altering device;
transforming the first sensor data obtained from the plurality of wireless sensors into one or more of first gait parameters, wherein the one or more of first gait parameters includes one or more of gait cycle duration, gait cadence, stride length, stride velocity, turning angle, stance, swing, loading, foot flat, pushing, double support, peak angular velocity, swing speed, strike angle, lift-off angle, swing width, 3D path length, maximum heel clearance, maximum toe clearance (foot with toes angled downward), minimum toe clearance, and second maximum toe clearance (foot with toes angled downward) while the person is wearing the gait-altering device;
receive from the plurality of wireless sensors, second sensor data comprising data obtained from the one or more sensors while the person is not wearing the gait-altering device, wherein the transferable housing is removed from the gait-altering device and attached to the at least one foot of the person;
transforming the second sensor data obtained from the plurality of wireless sensors into one or more of second gait parameters, wherein the one or more of second gait parameters includes one or more of gait cycle duration, gait cadence, stride length, stride velocity, turning angle, stance, swing, loading, foot flat, pushing, double support, peak angular velocity, swing speed, strike angle, lift-off angle, swing width, 3D path length, maximum heel clearance, maximum toe clearance (foot with toes angled downward), minimum toe clearance, and second maximum toe clearance (foot with toes angled downward) while the person is not wearing the gait-altering device;
analyze at least a portion of the first gait parameters and at least a portion of the second gait parameters wherein the analyzing at least comprises comparing at least a portion of the first gait parameters and the second gait parameters; and
determining, based on the analysis, a treatment plan and/or a modification of an existing treatment plan for the person involving use of the gait-altering device.

8. The system of claim 7, wherein the one or more processors comprise at least a portion of a cloud network.

9. The system of claim 7, wherein the plurality of wireless sensors comprise of at least an accelerometer, a gyroscope, a barometer, and a GPS detection device.

10. The system of claim 7, further comprising modifying an aspect of the gait-altering shoe based on at least a portion of the analyzed first gait parameters and/or second gait parameters, wherein modifying the aspect of the gait-altering shoe based on at least a portion of the analyzed first gait parameters and/or second gait parameters comprises providing a new wheel with a design based at least in part on the portion of the analyzed first gait parameters and/or second gait parameters.

* * * * *